(12) United States Patent
Barauskas et al.

(10) Patent No.: US 8,187,629 B2
(45) Date of Patent: May 29, 2012

(54) NON-LAMELLAR COMPOSITIONS OF DOPE AND P80

(75) Inventors: Justas Barauskas, Lund (SE); Fredrik Tiberg, Lund (SE)

(73) Assignee: Camurus AB, Lund (SE)

( * ) Notice: Subject to any disclaimer, the term of this patent is extended or adjusted under 35 U.S.C. 154(b) by 406 days.

(21) Appl. No.: 10/586,778

(22) PCT Filed: Jan. 21, 2005

(86) PCT No.: PCT/GB2005/000200
§ 371 (c)(1),
(2), (4) Date: Mar. 23, 2007

(87) PCT Pub. No.: WO2005/070392
PCT Pub. Date: Aug. 4, 2005

(65) Prior Publication Data
US 2007/0281030 A1   Dec. 6, 2007

(30) Foreign Application Priority Data
Jan. 23, 2004 (GB) .................................. 0401513.7

(51) Int. Cl.
*A61K 9/127* (2006.01)

(52) U.S. Cl. ........ 424/450; 424/400; 424/455; 514/937; 514/938

(58) Field of Classification Search ........................ None
See application file for complete search history.

(56) References Cited

U.S. PATENT DOCUMENTS

| 5,531,925 | A | * | 7/1996 | Landh et al. ............. 252/299.01 |
| 6,120,794 | A | * | 9/2000 | Liu et al. ....................... 424/450 |
| 2001/0031740 | A1 | * | 10/2001 | Unger et al. ..................... 514/44 |

FOREIGN PATENT DOCUMENTS

| WO | 97/11682 | | 4/1997 |
| WO | WO 97/11682 | * | 4/1997 |
| WO | 2005/014162 | | 2/2005 |
| WO | WO 2005/014162 A1 | | 2/2005 |

* cited by examiner

*Primary Examiner* — Robert A Wax
*Assistant Examiner* — Hasan Ahmed
(74) *Attorney, Agent, or Firm* — Nixon & Vanderhye P.C.

(57) ABSTRACT

The present invention relates to particulate compositions comprising at least 50% of dioleoyl phosphatidyl ethanolamine (DOPE) and 1 to 50% of Polysorbate 80 (P80). All parts are by weight relative to the sum of the weights of a+b and the compositions comprise non-lamellar particles or form non-lamellar particles when contacted with an aqueous fluid. The compositions have advantageous stability and low toxicity and the invention also relates to pharmaceutical compositions thereof.

16 Claims, 1 Drawing Sheet

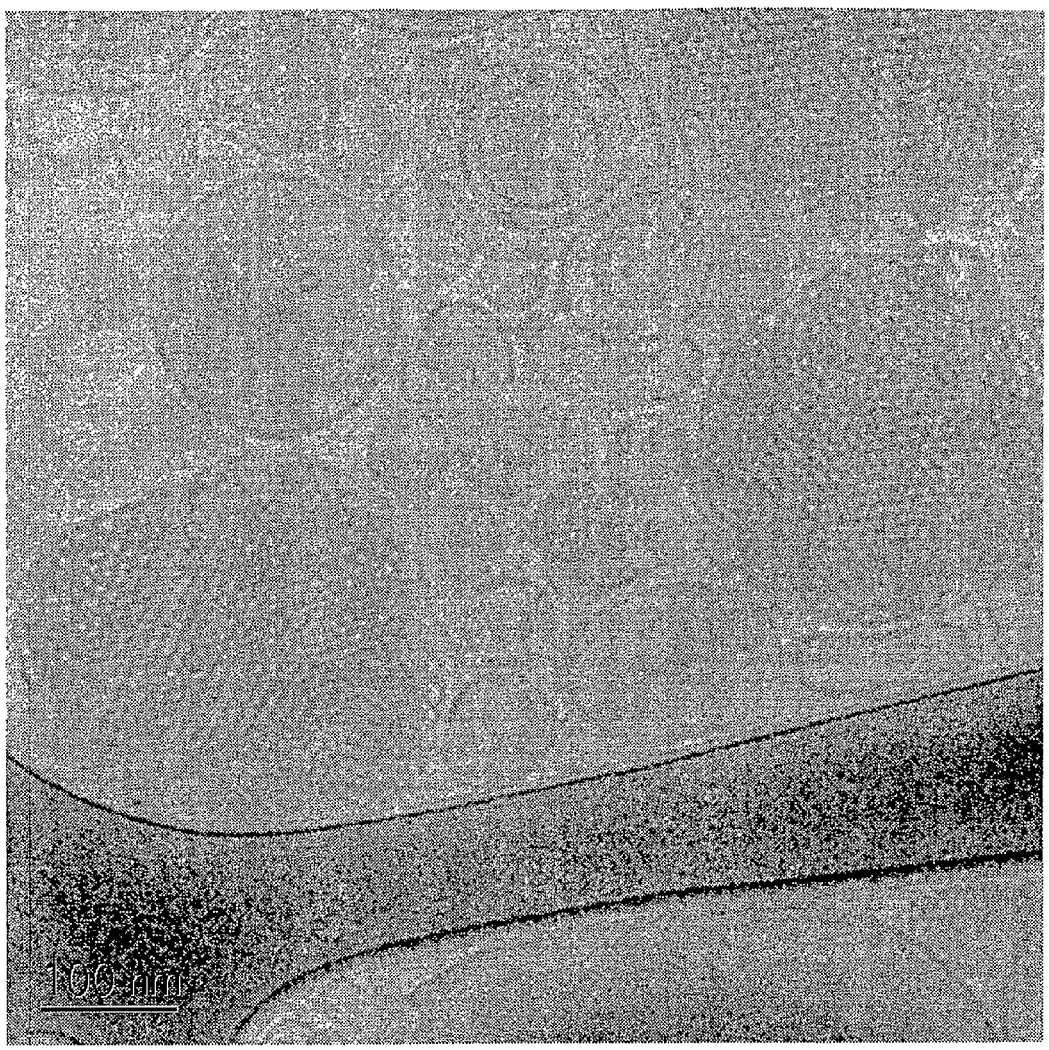

NON-LAMELLAR COMPOSITIONS OF DOPE AND P80

This application is the US national phase of international application PCT/GB2005/000200 filed 21 Jan. 2005 which designated the U.S. and claims priority to GB 0401513.7 filed 23 Jan. 2004, the entire content of each of which is hereby incorporated by reference.

The present invention relates to compositions useful in the protection, stabilisation and delivery of active agents. In particular, the invention relates to amphiphilic compositions and formulations, and active agent delivery systems based upon these.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ "sponge" phase which comprises a multiply interconnected three-dimensional bi-continuous network of bilayer sheets which lack the long-range order of the liquid crystalline phases. Depending upon their curvature, these phases may be described as normal (mean curvature towards the apolar region) or reversed (mean curvature towards the polar region). Where the spontaneous curvature of the lipid system is close to zero, the structures are typically lamellar, such as uni- or multi-lamellar vesicles/liposomes and where the spontaneous curvature is more negative or positive, micellar, cubic and hexagonal phases typically dominate.

The non-lamellar liquid crystalline and $L_3$ phases are thermodynamically stable systems. That is to say, they are not simply a meta-stable state that will separate and/or reform into layers, lamellar phases or the like, but are the thermodynamically stable form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area between polar and apolar regions. This has led to considerable investigation of non-lamellar phases particularly in controlled-release formulations and for solubilising compounds of relatively low solubility.

As discussed above, a bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk non-miscible phase would cause problems, such as in parenteral applications. Further control of a compound's release profile may also be achieved by such a dispersion of non-lamellar particles.

Liquid crystalline or $L_3$ phase can be in or near thermodynamic equilibrium with the excess solvent and may be dispersed into colloidally stable dispersions of non-lamellar particles. Such particles may be fully (i.e. thermodynamically) stable, or may gradually degrade, thereby providing control over the release profile for active agents formulated therewith. The formation of dispersions can be spontaneous or as the result of mechanical force such as shearing or ultrasound. These non-lamellar particles are of considerable interest in the delivery of active agents and have been proposed as carriers for many such actives.

The phase behaviour of systems of dioleoyl phosphatidyl ethanolamine (DOPE) and the PEG substituted distearoyl phosphatidyl ethanolamine, lipids DSPE-PEG (2000) and DSPE-PEG (750) were investigated by Johnsson et al. but have been found to form dispersions too unstable to be of value.

Known particles of liquid crystalline or $L_3$ interior phase may be formed by methods such as adding to this phase a solution of surface-phase forming agent, stirring to form a coarse dispersion and fragmenting the resulting mixture.

In order to assess the presence of a liquid crystalline phase, the prospective liquid crystalline material may be examined by use of small-angle X-ray diffraction (SAX), cryo-Transmission Electron Microscopy (cryo-TEM) or Nuclear Magnetic Resonance (HMR) spectroscopy studies. The sizes and size distributions of the dispersed particles may be examined by light scattering, particularly by use of laser light scattering instruments.

Dispersions containing active ingredients and particularly those for intravenous administration to the human or animal body are desirably colloidal, that is they should be of a particle size no greater than 10 μm, especially no greater than 5 μm and particularly no greater than 1 μm. If particles within the dispersion exceed this size then the dispersion may not be colloidally stable and there is a considerable risk of causing embolism when the preparation is administered intravenously. Furthermore, it is desirable that the distribution of particle sizes be narrow to maximise control over the release of any active agent. Where a particulate composition is to be administered by a method other than intravenously (e.g. orally, intramuscularly, subcutaneously, rectally or by inhalation), then the particles need not necessarily be colloidal but it remains advantageous to provide a well characterised and reproducible particle size distribution in order to control the rate of decomposition of the particles and/or release of the active agents.

The particle size of a particulate composition should also be stable to storage over a considerable period of time. If the distribution of particle sizes changes significantly then the effective transport rate for composition (e.g. due to diffusion and rate of release of any active agent) may be adversely affected. Of still greater concern is the stability of particle sizes in a colloidal dispersion for intravenous administration. If the particle size distribution of such a dispersion is not stable (e.g. to storage and distribution) then large particles may form over time and be dangerous when administered. Even if not directly dangerous, storage instability can cause significant varibility in pharmacokeinetics, dynamics and/or efficacy.

A method for the formation of dispersed particles of non-lamellar phase in solvents such as water is described in U.S. Pat. No. 5,531,925. Such particles have a non-lamellar liquid crystalline or $L_3$ interior phase and a lamellar or $L_3$ surface phase and may also contain active ingredients.

In addition to controlling particle size, it is desirable to maximise the proportion of particles which are in the desired, non-lamellar, phase in order to maximise the beneficial effects of this in terms of controlled release and reproducibility. The proportion of lamellar particles such as uni- or multi-lamellar vesicles should therefore be minimised.

Known methods for the formation of dispersed particles of non-lamellar phase are highly effective, but typically produce a relatively broad distribution of particle sizes and a certain proportion of "contaminant" lamellar vesicular particles. Increasing the proportion of fragmenting and/or stabilising agent (e.g. surfactant, copolymer and/or protein) in the formulation or increasing the energy input of the homogenisation process may be used to narrow the particle size distribution but at the expense of increasing the proportion of lamellar particles.

One limitation of non-lamellar compositions presently available or suggested is that they frequently rely upon lipids which are not well tolerated in vivo at high concentrations. In commonly used monoacyl glycerols (including the popular glyceryl monooleate—GMO) can be toxic at high concentrations, which can be dose-limiting. The possibility of toxicity from the lipid carrier can also limit the range of indications for which an active agent is used to those of a highly serous nature, where the risk of side-effects may be tolerated. It would, therefore, be a considerable advance to provide lipid compositions which were formable and stable as particulate dispersions, showed predictable non-lamellar phase behaviour and had decreased toxicity, (e.g. as seen from haemolysis indices and/or acute toxicity studies) when compared with widely used compositions (e.g. those including GMO). It would be of further advantage if such formulations were formable and highly stable as colloidal sized particle dispersions (e.g. of particles 0.05 to approximately 2 µm in diameter) and had a narrow, mono-modal, particle size distribution.

The present inventors have unexpectedly established that a mixture of 2 specific amphiphilic components is highly effective in forming stable non-lamellar dispersions and can show surprisingly low toxicity in vivo.

In a first aspect, the present invention therefore provides a particulate composition comprising;
a) at least 50% of dioleoyl phosphatidyl ethanolamine (DOPE); and
b) 1 to 50% of Polysorbate 80 (P80)
wherein all parts are by weight relative to the sum of the weights of a+b and wherein the composition comprises non-lamellar particles or forms non-lamellar particles when contacted with an aqueous fluid.

Preferred compositions of the present invention additionally contain at least one active agent as described herein and may contain a solvent (particularly water or an aqueous solvent or solvent mixture). The compositions may also contain suitable carriers, excipients, fillers, stabilisers and similar components.

In a further aspect, the present invention provides a pharmaceutical formulation comprising at least one composition of the invention and at least one pharmaceutically tolerable carrier or excipient.

The amphiphilic compositions of the invention comprise dioleoyl phosphatidyl ethanolamine (DOPE—component a), and the "structure swelling" agent Polysorbate 80 (P80—component b). Component b will also facilitate fragmentation of the composition. At least 50% (i.e 50-99%) by weight of the total amphiphilic components (a+b) should be DOPE and 1 to 50% P80.

Preferably the proportion of DOPE will be 60 to 95%, more preferably 65 to 90% and typically 80 to 90%. Correspondingly, the level of P80 should preferably be 5 to 40% by weight of a+b, more preferably 10 to 35% and most preferably 10 to 20%.

DOPE is such that when formulated alone in excess water it forms a reversed hexagonal phase. This can be easily established by preparing a mixture in water and analysing the phase behaviour by any of the techniques known and/or described herein (including small angle X-ray scattering (SAXS), polarising microscopy and/or cryo-transmission electron microscopy (cryo-TEM)).

Since DOPE is the dominant component in the composition, it is especially important that this component is biocompatible. Previously, many non-lamellar compositions have relied upon major structure forming components with relatively high acute toxicity, in order to provide the desired ordered structure and stability. By using the compositions of the present invention, the use of lipids with less than ideal biological properties can be reduced or even eliminated.

One measure of the biological activity of a lipid is its solubility in water or aqueous solutions. Components with relatively high aqueous solubilities maintain a higher equilibrium concentration of dissolved lipid monomer in solution and this can be at least partially responsible for the observed biological effects. The commonly used "glycerol monooleate" (GMO), for example, has an equilibrium water solubility of at least $10^{-7}$ M at room temperature and greater at physiological temperature. In contrast, DOPE has a solubility of around $10^{-10}$ M.

Polysorbate 80 (P80) is a common name for the polyoxyethylene sorbitan fatty acid ester PEG (20) sorbitan monooleate. This compound swells the lattice of DOPE allowing it to more readily adopt a dispersed particulate form.

Component b also acts as fragmentation agent and helps both in the control and stability of phase behaviour and in encouraging and stabilising the fragmentation of the non-lamellar phase into particles.

The particular choice of P80 as the structure swelling agent has been found to provide particulate dispersions of high stability.

Component b will be present at a level sufficient to facilitate the fragmentation of the DOPE phase structure and/or to stabilise the fragmented non-lamellar phase particles. Such fragmentation may be spontaneous or may require physical fragmentation such as by shearing and/or ultrasonication. The skilled worker will have no difficulty in assessing whether any composition contains sufficient fragmentation agents in view of the Examples herein.

The compositions of the present invention comprise non-lamellar particles or form such particles on contact with an aqueous fluid. Such a fluid may be a fluid for delivery to a subject (e.g. water or sterile saline) or may be a body fluid, particularly gastric fluid, intestinal fluid, fluid at mucosal surfaces or blood.

As use herein, the term "non-lamellar" is used to indicate a cubic, or hexagonal or $L_3$ phase or any combination thereof, as opposed to lamellar structures as found in lamellar phase or liposomes. Where a particle is described as having a non-lamellar phase or structure, this indicates that at least the particle interior has this structure. The particles will generally have two distinct regions, an internal region and a surrounding surface region. The surface region, even in a "non-lamellar" particle may be lamellar or crystalline and may be any phase ranging from highly a ordered crystalline or liquid crystal phase to a virtually orderless fluid layer.

The term "lamellar particles" is used herein to indicate vesicular particles (e.g. liposomes) characterised in that they comprise one or more outer lamellar bilayers of amphiphile, surrounding an inner solvent compartment.

In one aspect of the present invention, the compositions comprise non-lamellar particles. This indicates that of the (preferably colloidal) particles present, at least 50%, preferably at least 75% and most preferably at least 85% (as measured by volume) are non-lamellar (e.g. as judged by laser diffraction combined with cryo-TEM or SAXS). In an alternative aspect of the present invention, the compositions form non-lamellar particles on contact with an aqueous fluid. This indicates that upon contact with an aqueous fluid (as described herein) at least 50%, preferably at least 75% and most preferably at least 85% of the particles (as measured by volume) become non-lamellar particles.

Where an active agent is formulated in a composition of the invention, the active agent will frequently have an effect upon the phase behaviour of the structuring agent(s). For example, certain active agents (such as cyclosporin A) introduce greater negative curvature than DOPE and at high concentrations may cause the formation of highly negatively curved phases, such as the reversed micellar $L_2$ phase rather than a cubic or hexagonal liquid crystalline phase. Nonetheless, such an active agent may be formulated into, for example, a reversed hexagonal phase by formulation with an appropriate mixture of DOPE and P80; P80 having a less negative spontaneous curvature. By this method, the overall mixture provides the appropriate negative curvature to allow use in the compositions of the invention.

The skilled worker will be able to use standard methods to assess the degree of spontaneous curvature of any particular mixture or the effect on this by including an active agent. This might be done, for example, by studies of the bulk phase behaviour of the DOPE/P80 mixture in water and subsequent studies with varying concentrations of active agent included. The phases can be examined by any of the methods indicated herein (e.g. polarised light, SAXS, cryo-TEM etc.) and an appropriate blend of components chosen for each case. In some circumstances, where the effect of the active agent on the phase behaviour of the mixture is significant, the DOPE/P80 mixture chosen may not provide the desired non-lamellar phase in itself (e.g. may have too small or too great spontaneous curvature) but will generate this phase only when also formulated with the active agent. The equilibrium phase may thus change from, for example, cubic to hexagonal liquid crystalline phase upon addition of the active agent.

In a preferred embodiment, the compositions of the present invention comprise at least one active agent. Suitable active agents include human and veterinary drugs and vaccines, diagnostic agents, "alternative" active agents such as plant essential oils, extracts or aromas, cosmetic agents, nutrients, dietary supplements etc. Examples of suitable drugs include antibacterial agents such as β-lactams or macrocyclic peptide antibiotics, anti fungal agents such as polyene macrolides (e.g amphotericin B) or azole antifungals, anticancer and/or anti viral drugs such as nucleoside analogues, paclitaxel and derivatives thereof, anti inflammatories, such as non-steroidal anti inflammatory drugs, cardiovascular drugs including cholesterol lowering and blood-pressure lowing agents, analgesics, antidepressants including serotonin uptake inhibitors, vaccines and bone modulators.

In colloidal compositions, the average (mean) particle size will typically be in the range 0.1 to 0.6 μm, for example as determined by light scattering methods (e.g. laser diffraction). Preferably, no more than 1% of particles will be outside the range 0.05 to 1.5 μm, more preferably, not more than 0.1% will be outside this range, and most preferably no detectable (by laser diffraction) proportion of particles will be outside this range. In non-colloidal formulations the average particle size will typically be in the range 10 to 150 μm.

Furthermore, the colloidal formulations of the present invention are typically physically stable to storage over extended periods at ambient temperature. Such formulations should be essentially stable both in terms of phase behaviour and particle size for periods of at least 10 days at room temperature, more typically at least 3 months, preferably at least 6 months and more preferably 12 months or more. In contrast, known dispersions of similar particle size may have particle sizes stable for less than 10 days at room temperature.

A particle size distribution can be considered essentially stable to storage if the average particle size increases no more than two fold during the storage period. Preferably, the average size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period. In a highly preferred embodiment, the distribution of sizes of particles of the compositions of the invention alter in average particle size and particle size distribution width at half-height by no more than 10% and remain monomodal on storage for the periods indicated above.

It is particularly important in the case of colloidal dispersions for use in intravenous or intra-arterial administration that the particle size distribution be stable during storage and use. A composition containing even a relatively small component of non-colloidal particles may cause embolism, or at least unpredictable rates of release upon administration directly to the blood stream. Similarly, the controlled release of an active agent may be dependent upon a reliable particle size distribution in a composition for administration by any other route. Pharmaceutical, diagnostic and veterinary products are also desirably stable to storage for several months or the cost and availability of the product is significantly adversely affected.

The compositions of the present invention may be formed by preparing a dispersion of DOPE and P80 in a solvent (such as an aqueous solvent) and then optionally treating the dispersion with one or more cycles of heating and cooling.

The compositions of the present invention may be formed by preparing a dispersion of DOPE and P80 in a solvent (such as an aqueous solvent). This formulation may be prepared by established methods, such as those indicated in the present Examples and in U.S. Pat. No. 5,531,925, WO 02/02716, WO 02/068561, WO 02/066014 and WO 02/068562. The disclosures of these and all references cited herein are hereby incorporated herein by reference. Such methods include adding an amphiphile/water liquid crystal phase (such as DPOE in water) to an aqueous solution of fragmentation agent (P80) and either allowing natural fragmentation of the mixture or accelerating the process with, for example, mechanical agitation, vortexing, roto-stator mixing, high-pressure homogenization, microfluidisation and/or ultrasound.

The presence of particles in non-lamellar form will preferably be assessed from a set of cryo-transmission electron microscopy particle images, preferably showing a sample of more than 20, preferably more than 50 particles. The presence of non-lamellar particles may also be assessed by X-ray scattering experiments.

The particles may be concentrated (e.g. by ultrafiltration or dialysis) and/or dried, for example by spray drying, fluid bed drying or freeze drying. In the case of dried particles, the drying process may be followed by particle size enlargement through single or repeated agglomeration and granulation steps. The concentrated, dried and/or agglomerated particle formulations thus formed may be used as such or hydrated and/or dispersed to yield non-lamellar particle dispersions suitable for use in the delivery of active substances, especially in vivo. Such concentrated, dried and/or agglomerated particle formulations and the dispersions resulting from their re-suspension/hydration form a further aspect of the present invention.

The formulations of the present invention comprise at least one composition of the invention and at least one carrier or excipient. Where the formulation is a pharmaceutical formulation the carriers or excipients will be pharmaceutically tolerable.

The compositions may be formulated with conventional pharmaceutical carriers, diluents and/or excipients such as aqueous carriers (e.g. water for injections), binders, fillers, stabilizers, osmolality adjusting agents, effervescing agents, pH buffers and modifiers, viscosity modifiers, sweeteners, lubricants, emulsifiers, flavours, coating agents (e.g. gastric juice resistant coatings) etc. Formulations comprising a composition of the invention and at least one pharmaceutically acceptable carrier and/or diluent may be formulated in any known dosage form including as suspensions, powders, tablets, capsules, coated capsules, coated tablets, aerosols, suppositories, creams, transdermal patches, sprays etc. Where the composition of the invention has been dried, this may be formulated as a suitable form (such as a powder) for resuspension in an appropriate medium (such as purified water or a solution of physiological osmolality) prior to administration.

In one embodiment of the invention, the formulations are suitable to be administered parenterally (e.g by intramuscular, subcutaneous or intravenous injection or infusion). In an alternative embodiment, the formulations are suitable for administration by any other method including orally, by inhalation, topically (e.g. as a cream or eye drops), rectally etc.

The invention will now be further illustrated by reference to the following non-limiting Examples and the attached Figures, in which;

FIG. 1 shows a cryo-TEM image of non-lamellar particles of a coarse dispersion of DOPE and P80.

EXAMPLE 1

Amphiphilic Particles

A dispersion of cubic and lamellar particles was formed by mixing DOPE (Avanti Polar Lipids U.S.A., 0.80 g), and P80 (0.2 g) in deionized water (49.0 g) and agitate by magnetic stirrer for 24 hours.

FIG. 1 shows a cryo-transmission Electron Microscopy (cryo-TEM) image of non-lamellar particles of a coarse dispersion of DOPE:P80 at a ration of 80:20.

EXAMPLE 2

Stability

The phase behaviour of the dispersion prepared in Example 1 was examined before and after storage for 10 days at ambient temperature. No change in particle size or phase behaviour was seen.

EXAMPLE 3

Toxicity Testing 3.1 Heamolysis

The resulting dispersion (white) from Example 1 was thereafter homogenised in a microfluidizer at high pressure (350 bar) for 10 min (8 passes) at ambient temperature, autoclaved (120° C., 20 min) and cooled to room temperature.

The weight ratio DOPE:P80 was 80:20, dispersed in water to a total amphiphile concentration of 5 wt %. This solution was diluted with water to varying final concentrations.

The heamolytic effect of the dispersion at varying concentrations was measured. The dispersion was found to be non-heamolytic at concentrations of up to 1 wt % total amphiphile.

Cubic dispersions of glycerol monoolein were prepared by a corresponding method and tested for haemolytic effect under the same conditions. The GMO based dispersion showed significant haemolytic effects at concentrations as low as 0.1 wt % total amphiphile.

3.2 Pyrogenicity

A DOPE/P80 formulation was prepared as in Example 3.1 and was tested for pyrogenicity in a rabbit model. The composition was found to be non-pyrogenic up to doses of at least 5 ml/kg (5 wt % total amphiphile).

3.3 Acute Toxicity

DOPE/P80 and GMO based compositions were prepared as in Example 3.1 and tested for acute toxicity in a rat model.

The DOPE based cubic phase dispersion showed no acute toxicity in a dose dependant study with doses up to 10 ml/kg (10 wt % amphiphile).

The glycerol monoolein based cubic phase dispersions, on the other hand, were found to be toxic at corresponding lipid doses.

The invention claimed is:

1. A particulate composition comprising;
   a) at least 60% of dioleoyl phosphatidyl ethanolamine (DOPE); and
   b) 1 to 40% of Polysorbate 80 (P80),
   wherein all parts are by weight relative to the sum of the weights of a+b,
   wherein a and b form the total amphiphilic components, and
   wherein the composition comprises non-lamellar particles or forms non-lamellar particles when contacted with an aqueous fluid.

2. A particulate composition of claim 1 comprising an amphiphilic carrier formulation consisting of;
   a) at least 60% of dioleoyl phosphatidyl ethanolamine (DOPE);
   b) 1 to 40% of Polysorbate 80 (P80);
   c) optionally a solvent;
   wherein all parts are by weight relative to the sum of the weights of a+b and wherein the composition comprises non-lamellar particles or forms non-lamellar particles when contacted with an aqueous fluid and wherein the carrier formulation exhibits no toxicity in rats at a level of up to at least 1000 mg of components a+b per kg of subject.

3. A particulate composition of claim 1 comprising an amphiphilic carrier formulation consisting of;
   a) at least 60% of dioleoyl phosphatidyl ethanolamine (DOPE);
   b) 1 to 40% of Polysorbate 80 (P80);
   c) optionally a solvent;
   wherein all parts are by weight relative to the sum of the weights of a+b and wherein the composition comprises non-lamellar particles or forms non-lamellar particles when contacted with an aqueous fluid and wherein the carrier formulation exhibits no pyrogenicity when dosed parenterally in rabbits at a level of up to at least 5 ml of a 5% dispersion of components a+b per kg of subject.

4. A composition as claimed in claim 1 additionally comprising at least one active agent.

5. A composition as claimed in claim 1 comprising at least 50% non-lamellar particles.

6. A composition as claimed in claim 1 which forms at least 50% non-lamellar particles upon contact with an aqueous fluid.

7. A composition as claimed in claim 6 wherein said aqueous fluid is a body fluid.

8. A composition as claimed in claim 1 wherein said particles have an average particle size of 10 to 150 µm.

9. A composition as claimed in claim 1 wherein said particles are colloidal.

10. A composition as claimed in claim 9 wherein said particles are stable in terms of phase behavior and particle size to storage at room temperature for at least 10 days.

11. A composition as claimed in claim 1 in the form of a dry powder.

12. A pharmaceutical formulation comprising a composition as claimed in claim 1.

13. A formulation as claimed in claim 12 further comprising at least one pharmaceutically tolerable carrier or excipient.

14. The composition of claim 1 comprising;
a) 60 to 95% of dioleoyl phosphatidyl ethanolamine (DOPE); and
b) 4 to 40% of Polysorbate 80 (P80)
wherein all parts are by weight relative to the sum of the weights of a+b.

15. The composition of claim 2 comprising;
a) 60 to 95% of dioleoyl phosphatidyl ethanolamine (DOPE); and
b) 4 to 40% of Polysorbate 80 (P80)
wherein all parts are by weight relative to the sum of the weights of a+b.

16. The composition of claim 3 comprising;
a) 60 to 95% of dioleoyl phosphatidyl ethanolamine (DOPE); and
b) 4 to 40% of Polysorbate 80 (P80)
wherein all parts are by weight relative to the sum of the weights of a+b.

* * * * *